United States Patent [19]

Krzyminski

[11] Patent Number: 5,646,735
[45] Date of Patent: Jul. 8, 1997

[54] HAND-HELD INSTRUMENT FOR REFLECTION MEASURING OF OPTICAL DENSITY AND COLOR ON PRINTED SHEETS

[76] Inventor: Harald Krzyminski, Wiesbadener Strasse 27, D-61462 Konigstein, Germany

[21] Appl. No.: 539,174

[22] Filed: Oct. 4, 1995

[30] Foreign Application Priority Data

Oct. 7, 1994 [DE] Germany ............... 44 35 893.8

[51] Int. Cl.$^6$ ........................................... G01J 3/46
[52] U.S. Cl. ........................................... 356/402
[58] Field of Search ........................ 356/402, 405, 356/406, 407, 326, 328; 364/498, 526

[56] References Cited

U.S. PATENT DOCUMENTS

| | | | |
|---|---|---|---|
| 4,961,646 | 10/1990 | Schrammli et al. | 356/328 |
| 5,319,437 | 6/1994 | Van Aken et al. | 356/328 |
| 5,373,364 | 12/1994 | Krzyminski | 356/405 |
| 5,394,237 | 2/1995 | Chang et al. | 356/328 |
| 5,400,138 | 3/1995 | Peterson et al. | 356/402 |
| 5,426,508 | 6/1995 | Schrammli | 356/402 |

FOREIGN PATENT DOCUMENTS

| | | |
|---|---|---|
| 0149424 | 7/1985 | European Pat. Off. . |
| 0299445 | 1/1989 | European Pat. Off. . |
| 0453830 | 10/1991 | European Pat. Off. . |
| 2456541 | 7/1978 | Germany . |
| 4318637 | 6/1994 | Germany . |
| 4305968 | 9/1994 | Germany . |

*Primary Examiner*—F. L. Evans
*Attorney, Agent, or Firm*—Webb Ziesenheim Bruening Logsdon Orkin & Hanson, P.C.

[57] ABSTRACT

To enable top illumination densitometers in the form of a hand-held instrument to be used not only for measuring light reflections but also for transmission of the test data to a computer, a hand-held instrument is provided comprising an instrument housing with a measuring head and an electronic control unit in the housing for converting the values measured in the measuring plane of the sheet. The housing contains an electronic computer input system connected to the electronic control unit, at least one click knob operable externally on the housing, and a control element for the inputs to the computer input system and a junction box for an interface for transmission of the measured data converted in the electronic control unit into signals to a computer.

7 Claims, 4 Drawing Sheets

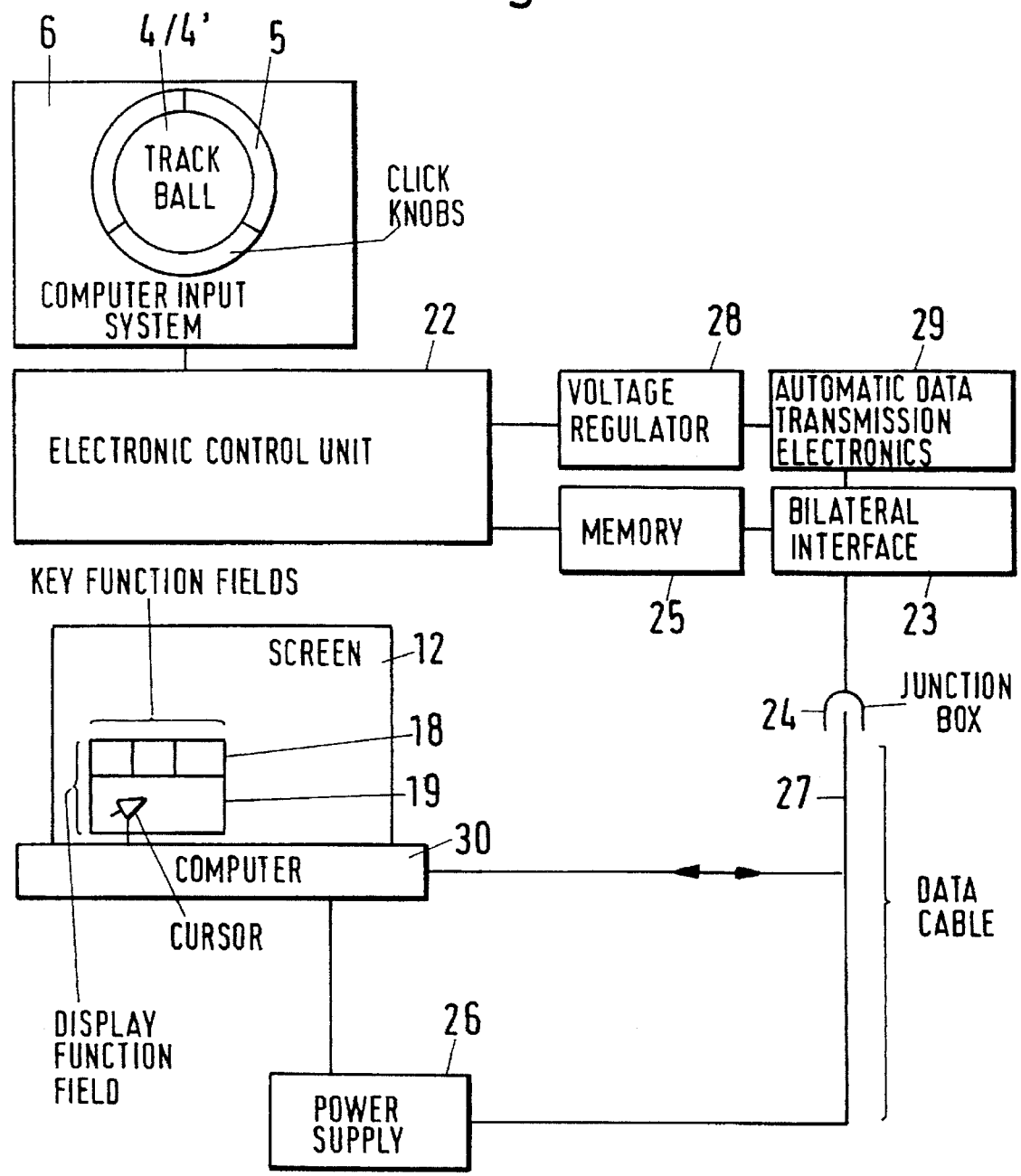

HAND-HELD INSTRUMENT FOR REFLECTION MEASURING OF OPTICAL DENSITY AND COLOR ON PRINTED SHEETS

BACKGROUND OF THE INVENTION

1. Field of the Invention

The present invention relates to a hand-held instrument for reflection measuring optical density and colour on printed sheets.

2. Description of the Prior Art

Instruments of this type are used in the printing industry in the form of colour measuring instruments and top colour illumination densitometers for controlling the colour flow in printing machines, particularly in multicolour screen printing.

Densitometers and colour measuring instruments of this type are known, for example, from European Patent 0 299 445 and German Patent 43 18 637. The essential components of instruments of this type are the housing, a display field for displaying the measured values, operating elements in the form of switches and keys, an electronic control unit arranged within the housing and a measuring head containing all mechanical and optical components required for recording the measured value. Components of this type, in addition, individually, have been described in closer detail in German Patent Application 43 05 968 (corresponding to U.S. Pat. No. 5,373,364). Instruments of the afore-described type increasingly are used in connection with computers in such a way that the measured values are transmitted to the computer and are further evaluated with the aid of software programs to be graphically displayed on the screen. The computer is operated by a keyboard and, increasingly, by additional input devices.

The two most commonly used input devices are those which are designated by the technical language mouse and trackball. Mouse and trackball are connected to the computer by means of a cable. However, a few types thereof also communicate with the computer by infra-red pulses or high-frequency radio signals. Essentially, mouse and trackball comprise a ball which, by moving it, can position a cursor at any desired point of the computer screen. In addition, mouse and trackball are provided with one or more click knobs conveying function commands to the computer. Mouse and trackball are distinguished from one another by a different arrangement of the ball on the housing. Concerning the mouse, the ball is arranged on the bottom side thereof and is moved on the tabletop by shifting the mouse, whereas in the trackball the ball is arranged on the upper side and can be moved in all directions by the operator's finger. Both input devices operate in such a way that the movement of the ball is transmitted to two optoelectronic elements transmitting the required displacment signals for the cursor in the X and Y directions to the screen.

The principle of operation of an electromechanically operating converter element converting a rotary movement to electric signals is described in German Patent Application 24 56 541 according to which the rotary movement of one or two wheels arranged at the bottom side on the converter element is transferred to a slotted aperture to which light is applied and is transmitted by a light pulse to a photocell.

According to a special design of the trackball, the ball is replaced by a rocking switch tiltable in all directions. Ball and rocking switch have equivalent functions so that the following description applies to both types even if no express reference is any longer made thereto. In connection with special software programs mouse and trackball contribute to a sustantially simplifying and expediting the operation of the computer, with the functional fields being displayed on the screen the functions of which can be easily recognized by the operator by letters or symbols. As soon as the cursor has been positioned in the desired functional field with the aid of the ball, the function as displayed can be performed by one of the click knobs. However, the operating comfort provided by mouse and trackball is substantially restricted if it is also to be used for measurements of the afore-mentioned type as in that case, in addition to the input device also the hand-held measuring instrument is to be used, i.e. both instruments will have to be alternatingly taken into the operator's hand.

SUMMARY OF THE INVENTION

It is the primary object of the invention to provide and improve a hand-held measuring instrument of the afore-indicated type in such a way that for reflection measuring density and colour at any desired computer conversion, such an operating comfort be insured for the measuring process itself and for the computer conversion. The above and other objects are accomplished according to the invention with a hand-held instrument for measuring reflections on a printed sheet extending in the measuring plane, which comprises an instrument housing with a measuring head and an electronic control unit arranged in the housing for converting the values measured in the measuring plane of the sheet.

The housing contains an electronic computer input system connected to the electronic unit, at least one click knob operable externally on the housing, a control element for the inputs to the computer input system, and a junction box for an interface for transmitting the signals of the measured values converted in the electronic control unit to a computer.

Thanks to the design of the hand-held measuring instrument according to the invention, the functions of a trackball system are directly integrated into the hand-held measuring instrument so that only the hand-held measuring instrument is to be operated in the usual way, with the same hand operating the hand-held measuring instrument being able to operate at the same time the computer input system irrespective of the point of the sheet to be measured at which the hand-measuring instrument is located.

The instrument according to the present invention involves an additional essential advantage. Measurements of the density and colour, frequently, are used in the measuring fields of printing control strips. Printing control strips of this type are used for controlling the color flow on printing machines. They are printed at the edge of the printing sheet, permitting in their colored measuring. fields a control and coordination of the individual colors involved in multicolour prints. In offset printing machines the printing width is subdivided into several color planes the color flow of which can be controlled independently of one another, meaning that the printing control strips extend across the entire sheet width and that the density values measured in the various control fields are to be associated to special color planes. This association, hitherto, has been effected by so-called scan densitometers able to scan, in one run, the entire length of the printing control strip by a movable measuring head, and to recognize the position thereof from any measuring field. In this connection, reference is made to European Patent Application 0 149 424.

Scan densitometers of this type thus provide the measured values which, in addition, are furnished with a position indication of the measured control field. In connection with a computerized evaluation, scan densitometers provide on the screen of the computer colour profiles in which, for example, the density of a printing color is applied in the form of a bar diagram over the row of the color planes. For a detailed description, reference is also made to the European Patent Application 0 453 830.

However, in view of the complicated handling, evaluations comparable to those of scan densitometers, substantially cannot be performed by a conventional hand-densitometer and a separately arranged input device. Still, operation is improved by the hand-held densitometer comprising an integrated trackball system according to the invention to such an extent that in connection with a suitable computer program also such complex measurements can be carried out. The measurement and transmission can be further simplified and expedited if the measurement is released by one of the click knobs and the transmission of the measured value is effected automatically not requiring any additional steps for which purpose suitable electronic components are provided on the electronic unit of the measuring instrument.

The same process can be used if in place of printing control strips, for example, test data is to be evaluated. Such test data comprises numerous measuring fields of different shape which, after printing, permit the quality of a printing machine to be rated in a diffentiated way. For that reason, test data is preferably used during final acceptance of new printing machines and for optimizing the adjustment of a printing machine in general. The numerous measuring fields can be evaluated in a particularly efficient way by a suitable software program. By displaying the measuring fields of the test data on the screen and by incorporating the same into a software program, access and measurement of the control fields and evaluation thereof can be substantially simplified as the measuring device according to the invention now is equipped with an integrated computer input system.

BRIEF DESCRIPTION OF THE DRAWINGS

The above and other features, objects and advantages of this invention will become more apparent from the following detailed description of preferred embodiments, taken in conjunction with the accompanying drawings, wherein

FIG. 6 is a block diagram of the hand-held measuring instrument according to FIG. 4.

DETAILED DESCRIPTION OF THE PREFERRED EMBODIMENTS

The hand-held measuring instrument comprises a housing 1 with a measuring head 2 and an electronic control unit 22 arranged within the housing 1 for converting the measured values as shown in FIGS. 1,4,5 and 6.

Figure 1:
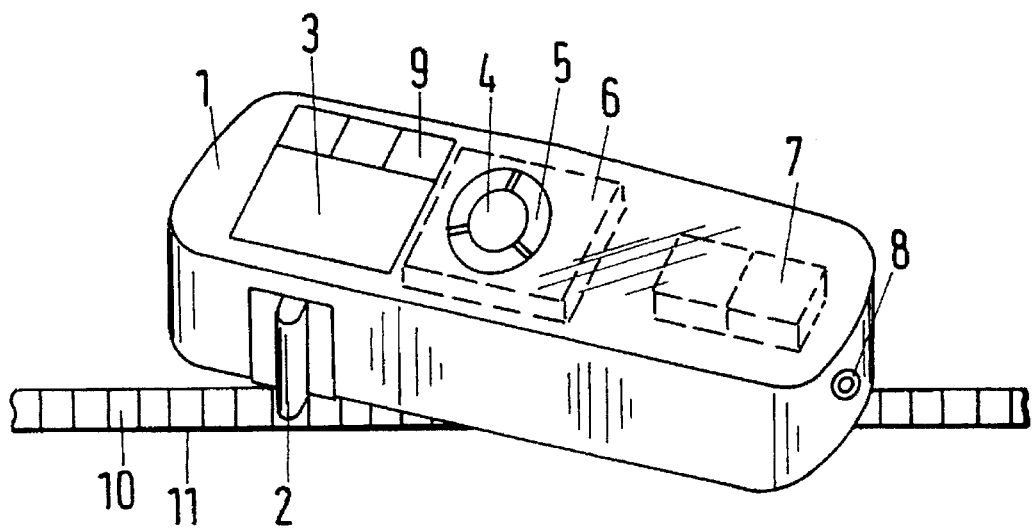
FIG. 1 is a perspective view of a hand-held measuring instrument comprising an integrated computer input system arranged above a printing control strip.

FIG. 1 shows a form of embodiment of the instrument of the invention according to which a trackball 4 for the displacement of the cursor is arranged in a manner conveniently accessible under the structural principle of the trackball on the upper side of the housing 1 with the measuring head 2 and the display field 3. Arranged about the ball are click knobs 5 by way of which functional commands can be given to the computer. Ball 4 and click knobs 5 are the only operating elements of the complete computer input system 6 visible on the housing, in which input system has an electronic control unit and conventional optoelectronic elements for recovering the signals of displacement. In order that the displacement signals of the computer input system 6, functional commands of the click knobs 5 and measured values of the measuring instrument can be transmitted to the computer, the measuring instrument according to the invention is furnished with electronic components 7 and a junction box 8 for an interface which in that case is unidirectional. With the measuring instrument so equipped, the operator is no longer required to permanently change over from the input device to the measuring instrument; he is now able to readily operate both the knobs 9 of the measuring instrument and the click knobs plus ball at the same time. In this respect, reference is made to the block diagram according to FIG. 5 intended for a so-called unidirectional way of operation.

Figure 2:
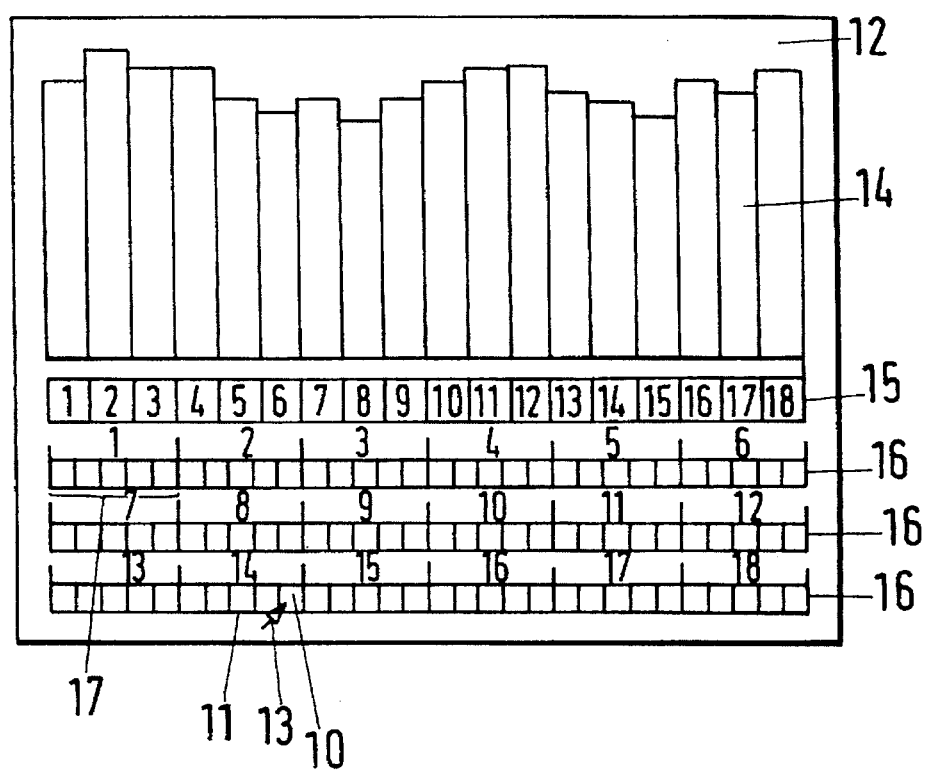
FIG. 2 is a perspective view of a computer screen showing printing control strip, color plane row and color profile.

As mentioned in the afore-going, practically no evaluation comparable to that of scan densitometers can be obtained by a conventional hand-held densitometer and a separately associated input device in view of the complex handling thereof. However, the operation is improved by a hand-held densitometer comprising an integrated trackball system according to the invention to such a degree that in connection with a suitable computer program complex measurements of this type can be performed. For this purpose, as shown by FIG. 2, the printing control strip 11 with the measuring fields 10 thereof, is displayed on the screen 12 of the connected computer, with the colored display permitting the distinction of the individual measuring fields. The measuring fields with the aid of the software program are associated to predetermined color planes of the printing machine. The control field selected for measuring is marked by the cursor 13 from the densitometer. Then the control field corresponding to the computer image is measured on the printing control strip of the printing sheet. The measured value in this way provided with a position indication can now be displayed on the screen in a color profile 14 over the color row 15 in the previously described way, with an illustration separated by printing colors being generally preferred.

The printing control strips frequently having a length of more than one meter, whereby the control fields thereof can be adequately displayed on the screen by subdividing them into two or more sections 16 and superposing the said sections as shown in FIG. 2. As both the printing control strip displayed on the screen and the strip as printed are subdivided into numbered segments 17, retrieval of the measuring field on the printed control strip as selected by the cursor does not involve any difficulties.

The operation of the measuring instrument as such can be improved if the computer input system 6 (FIG. 1) according to the invention is combined with a matrix display 3'(FIG. 5) forming the display field 3 (FIG. 1) and being capable to show graphical illustrations. In addition to the most widely used seven-segment and alphanumeric displays, occasionally, also matrix displays are used on densitometers and colour measuring instruments. However, the usefulness therof is limited as long they operate in connection with keys or rotary switches. It is only with the trackball 4 that a cursor can be randomly moved on the display in the X and Y directions, thereby substantially increasing the displayable functional density and simplifying and expediting the access of the functions. Working with the cursor controlled by the trackball on the matrix display 3' of the measuring instrument is especially advantageous if used in connection with graphical illustrations. This will provide similar manipulating capabilities, such as up- and down-scaling, fading in etc. otherwise offered only by the computer screen.

Figure 3:
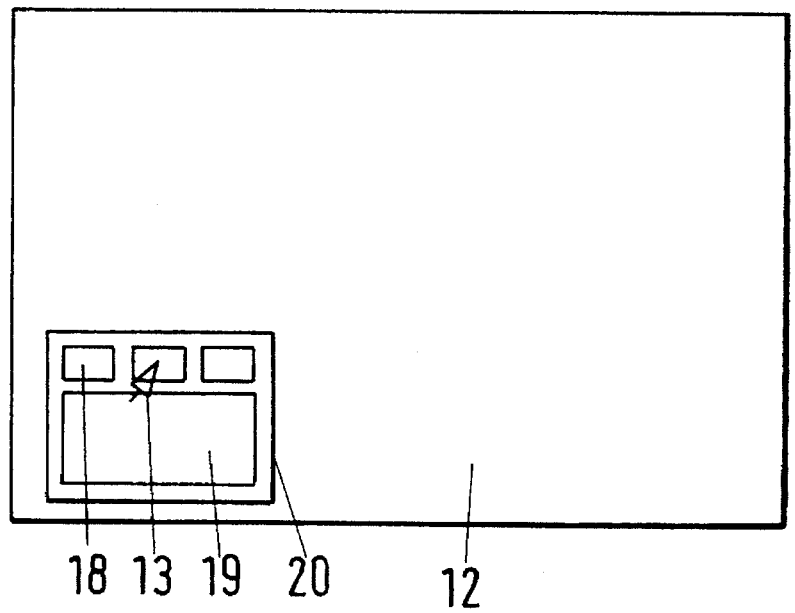
FIG. 3 equally is a view of a computer screen having a function window displayable in a corner for a hand-held measuring device according to FIG. 4.
Figure 4:
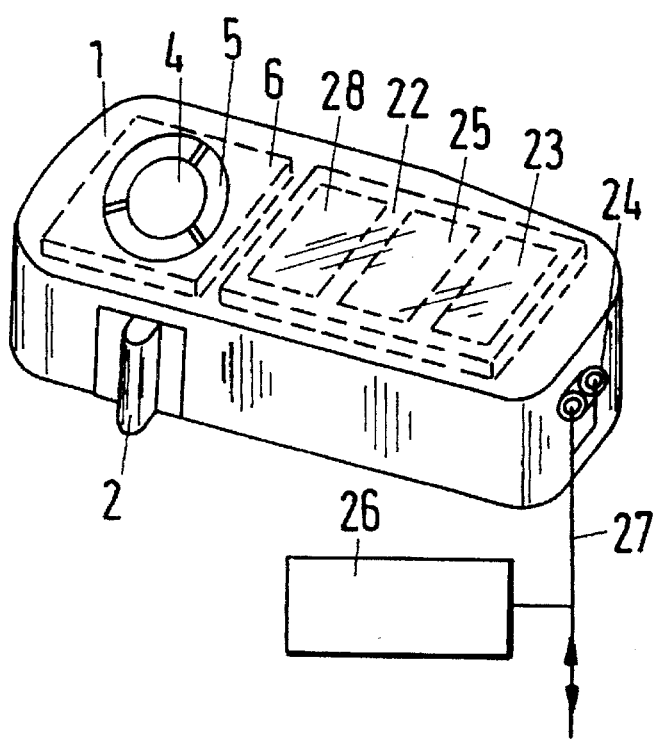
FIG. 4 is a perspective view of a special form of embodiment of the hand-held measuring instrument.

A completely new type of hand-held measuring instruments will be obtained if the knobs 9 normally provided on the measuring instrument and the display field 3 are replaced with the aid of the computer input system 6 assembled in the measuring instrument. Not only will this result in an additionally simplified operation but also in a less expensive manufacture of the measuring instrument according to the invention. Provision is made that the switching functions of the knobs 9, as shown in FIG. 3, are displayed by functional fields 18 on the screen 12 of the computer. Easy acces to the desired system function is provided by the trackball 4 (FIG. 1) and the cursor 13, and activation thereof is by one of the click knobs 5 (FIG. 1). The display field 3 usually provided in the measuring instrument is replaced by a corresponding display field 19 on the screen of the computer. The functional fields 18 of the knobs and of the display field 19, feasibly, are combined in a so-called window 20 and are arranged in one of the corners of the screen 12 in order to save as much place as possible for the remaining displays on the screen. FIG. 4 shows such a measuring instrument reduced to the following elements: housing 1, electronic control unit 22 with measuring head 2, computer input system 6 with ball 4 and click knobs 5 which compared to the conventional designs can be of a substantially more compact and less weighty construction. This will require that the usual unidirectional interface permitting the data transmission only in the one direction from the measuring instrument to the computer, be replaced by a bidirectional interface established by the interface module 23 on the electronic control unit 22 and a junction box 24 (see FIG. 6) thereby enabling the function orders of the computer to be transmitted to the measuring instrument. In the measuring instrument, the electronic control unit 22 is to be supplemented by a memory 25 taking up the functional commands coming from the computer, making them available for the control of the measuring instrument until they are replaced by new functional commands of the computer.

Another design of the bidirectional interface resides in that the power supply for the measuring instrument is performed by the power unit card 26 of the computer. The power supply to the measuring instrument can be effected via two additional cores of the data cable 27 so that no second cable is required that would affect the handling of the measuring instrument. For keeping constant and adapting the electric voltage to the electronic control unit 22 of the measuring instrument suitable electronic components 28 are provided. As the power supply to the measuring instrument is performed from the computer, the rechargeable accumulator otherwise normally assembled in the measuring instrument and the otherwise required charging device will be eliminated. The charging condition of the accumulator is no longer to be supervised by the operator, thereby eliminating the replacement and discharge of the accumulators having a limited life only. At the same time weight and costs are further reduced.

Figure 5:
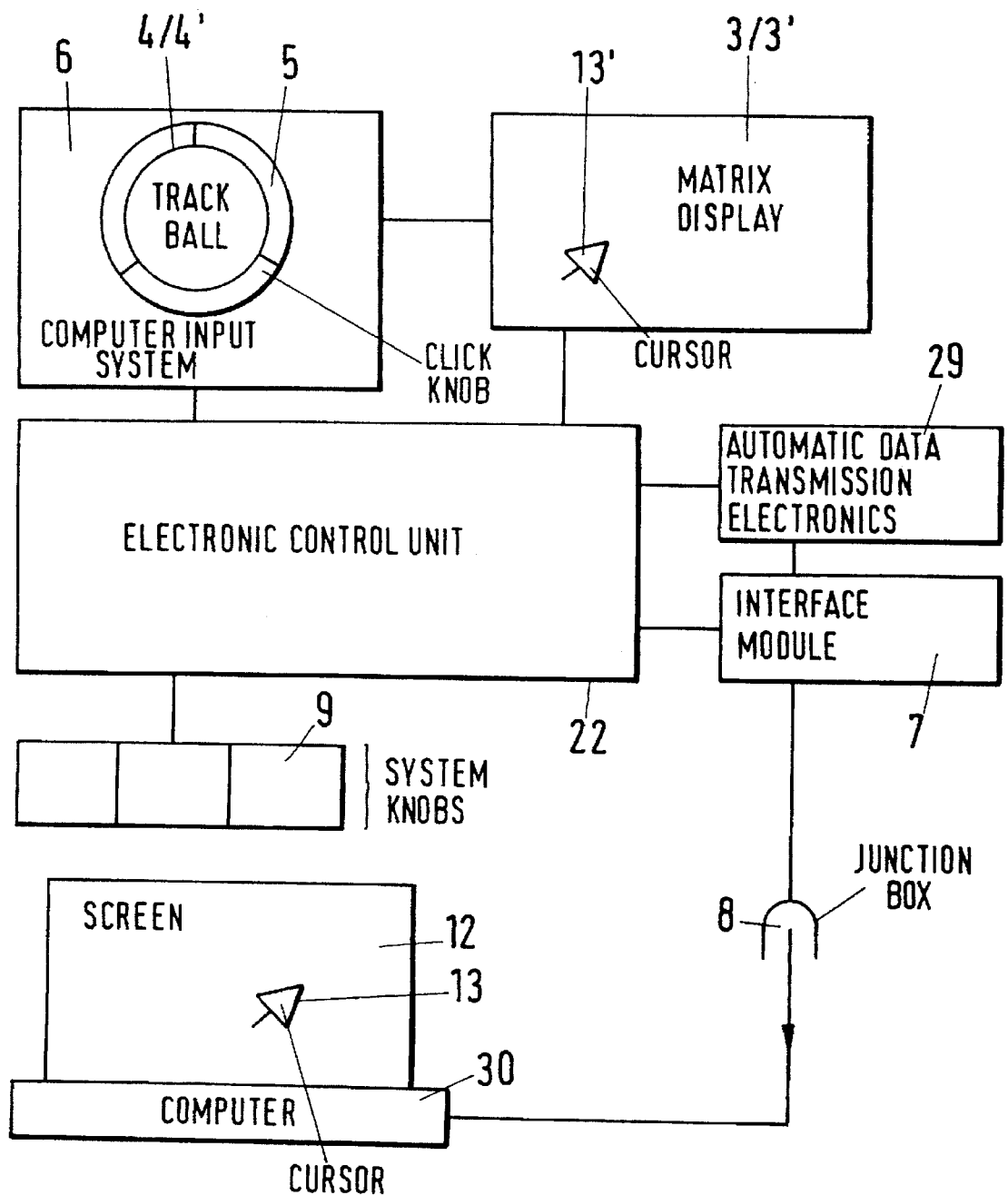
FIG. 5 is a block diagram of the hand-held measuring instrument according to FIG. 1.

FIG. 5 shows a block diagram disclosing the association of the components of the measuring instrument according to FIG. 1 to the computer. The computer 30 with the screen 12 and the cursor 13, through the junction box 8 and the interface module 7, is connected to the electronic control unit 22 of the measuring instrument. Additionally connected to the electronic control unit 22 are the computer input system 6 integrated into the measuring instrument with the accessible control element 4 and the trackball 4', respectively, and the click knobs 5, the display field 3 and the matrix display 3' capable to show graphical illustrations, with the cursor 13', the system knobs 9 and the electronic components 29 for the automatic data transmission.

FIG. 6 shows a block diagram illustrating the association of the components of the measuring instrument of FIG. 4 to the computer. The computer 30 with the screen 12, the key function fields 18, the display function field 19 and the cursor 13, through the data cable 27, the junction box 24, the bilateral interface module 23 and a memory 25 is connected to the electronic control unit 22 of the measuring instrument. Also connected to the electronic control unit 22 are the computer input system 6 integrated into the measuring instrument with the accessible control element 4 or the trackball 4', respectively, and the click knobs 5, the power supply card 26 of the computer and the electronic modules 28 for adapting and keeping constant the electric voltage. The conventional elements arranged in housing 1 of known top illumination densitometers for converting the measured interest in the present invention have not been shown.

What is claimed is:

1. A hand-held instrument for reflection measuring of optical density and colour on a printed sheet, comprising:

an instrument housing;

a measuring head and an electronic control unit provided in the housing for converting the values measured in the measuring plane of the printed sheet;

an electronic computer input system connected to the electronic control unit in the housing, said computer input system including at least one click knob operable externally on the housing, and a control element for the inputs to the computer input system; and a junction box for an interface for transmission of the measured data converted into signals in the electronic control unit to a computer.

2. The hand-held instrument of claim 1, wherein the control element is a trackball.

3. The hand-held instrument of claim 1, wherein the control element is a mercury switch tiltable in all directions.

4. The hand-held instrument of claim 1, wherein the computer input system has an additional click knob for the start of the measurement, and wherein the electronic control unit has electronic elements for the automatic transmission of the measuring data to the computer.

5. The hand-held instrument of claim 1, wherein a maxtrix display capable of displaying graphical illustrations and being connected to the electronic control unit and the computer input system is visibly installed on the housing.

6. The hand-held instrument of claim 1, wherein said junction box interface is bidirectional for reciprocal interchange of data between the computer and the measuring instrument, and wherein another interface element and memory are arranged between the junction box and the electronic control unit.

7. The hand-held instrument of claim 6, wherein the junction box is connected to a power line of the computer and wherein the electronic control unit includes electronic elements for adaptating and keeping the voltage constant.

* * * * *